United States Patent
Lijun (10) Patent No.: US 9,254,235 B2
(45) Date of Patent: Feb. 9, 2016

(54) MEDICAL HEAD RESTRAINT AND MEDICAL BED SYSTEM USING THE SAME

(75) Inventor: Wang Lijun, Dalian (CN)

(73) Assignees: KABUSHIKI KAISHA TOSHIBA, Tokyo (JP); Toshiba Medical Systems Corporation, Ottawar-shi (JP)

(*) Notice: Subject to any disclaimer, the term of this patent is extended or adjusted under 35 U.S.C. 154(b) by 274 days.

(21) Appl. No.: 12/856,943

(22) Filed: Aug. 16, 2010

(65) Prior Publication Data

US 2011/0035882 A1 Feb. 17, 2011

(30) Foreign Application Priority Data

Aug. 17, 2009 (CN) .......................... 2009 1 0167040

(51) Int. Cl.
- *A47B 13/00* (2006.01)
- *A61G 13/12* (2006.01)
- *A61B 6/04* (2006.01)

(52) U.S. Cl.
CPC ............ *A61G 13/121* (2013.01); *A61B 6/0421* (2013.01); *A61G 13/1235* (2013.01)

(58) Field of Classification Search
CPC ........... A61G 1/00; A61G 1/04; A61G 1/048; A61G 7/072; A61G 7/065; A61G 7/1073; A61G 7/1082; A61G 7/1086; A61G 7/1084; A61G 7/1088; A61G 13/12; A61G 13/1215; A61G 13/122
USPC ............................... 5/601, 621–623, 630, 632
See application file for complete search history.

(56) References Cited

U.S. PATENT DOCUMENTS

| | | | | |
|---|---|---|---|---|
| 1,279,120 A * | 9/1918 | Kellogg | ......................... | 607/115 |
| 2,398,940 A * | 4/1946 | Jones | .................. | 5/622 |
| 2,766,463 A * | 10/1956 | Bendersky | ....................... | 5/623 |
| 3,020,909 A * | 2/1962 | Stevens | ........................... | 602/39 |
| 4,836,523 A * | 6/1989 | Englander | ......................... | 5/623 |
| 5,177,823 A * | 1/1993 | Riach | ................................ | 5/636 |
| 5,312,323 A * | 5/1994 | McAninch | ...................... | 602/32 |
| 5,433,220 A | 7/1995 | Kostich | | |
| 5,461,739 A * | 10/1995 | Falbo, Sr. | ........................... | 5/607 |
| 5,742,962 A * | 4/1998 | Yoshino et al. | ................... | 5/623 |

(Continued)

FOREIGN PATENT DOCUMENTS

| | | |
|---|---|---|
| JP | 53-20572 | 7/1976 |
| JP | 58-79277 | 5/1983 |

(Continued)

OTHER PUBLICATIONS

Chinese Office Action issued Feb. 16, 2012 in Patent Application No. 201010256813.9 with English Translation.

(Continued)

*Primary Examiner* — David E Sosnowski
(74) *Attorney, Agent, or Firm* — Oblon, McClelland, Maier & Neustadt, L.L.P.

(57) ABSTRACT

According to one embodiment, a head restraint attached to a top of a bed of one of a medical image diagnosis apparatus and a medical treatment apparatus, the head restraint comprises a headrest portion configured to allow a head of an object to be placed thereon, with the object being placed on the top, and an arm up holder configured to be detachable from the headrest portion and place an arm of the object near one of a vertex of the head of the object and a temple of the head when the head of the object is placed on the headrest portion.

14 Claims, 7 Drawing Sheets

(56) References Cited

U.S. PATENT DOCUMENTS

| | | | |
|---|---|---|---|
| 5,771,512 A * | 6/1998 | Kurakake et al. | 5/623 |
| 6,151,734 A * | 11/2000 | Lawrie | 5/640 |
| 6,202,231 B1 * | 3/2001 | Heimbrock et al. | 5/623 |
| 6,371,119 B1 * | 4/2002 | Zadini et al. | 128/845 |
| 6,948,502 B2 * | 9/2005 | Berger et al. | 128/845 |
| 7,017,209 B1 | 3/2006 | De Jong et al. | |
| 7,080,420 B2 * | 7/2006 | Damron | 5/640 |
| 7,263,733 B2 * | 9/2007 | Fujita et al. | 5/601 |
| 7,761,943 B2 * | 7/2010 | Roleder et al. | 5/622 |
| 7,882,583 B2 * | 2/2011 | Skripps | 5/621 |
| 8,234,731 B2 * | 8/2012 | Skripps | 5/622 |
| 8,261,385 B2 * | 9/2012 | Mazzei et al. | 5/638 |
| 2011/0035882 A1 * | 2/2011 | Lijun | 5/601 |

FOREIGN PATENT DOCUMENTS

| | | |
|---|---|---|
| JP | 62-201141 | 9/1987 |
| JP | 62-213735 A | 9/1987 |
| JP | 64-58245 A | 3/1989 |
| JP | 1-153142 | 6/1989 |
| JP | 1-153143 | 6/1989 |
| JP | 10-14910 | 1/1998 |
| JP | 2003-102715 | 4/2003 |
| JP | 2003-135446 | 5/2003 |
| JP | 2004-65517 | 3/2004 |
| JP | 2006-115905 | 5/2006 |
| JP | 2006-247103 | 9/2006 |
| JP | 2009-321 | 1/2009 |
| JP | 2009-207835 | 9/2009 |

OTHER PUBLICATIONS

Combined Chinese Office Action and Search Report Issued Nov. 27, 2012 in Patent Application No. 201010256813.9 (with English translation).

Japanese Office Action issued Mar. 11, 2014, in Japan Patent Application No. 2010-181857 (with English translation).

* cited by examiner

MEDICAL HEAD RESTRAINT AND MEDICAL BED SYSTEM USING THE SAME

CROSS-REFERENCE TO RELATED APPLICATIONS

This application is based upon and claims the benefit of priority from Chinese Patent Application No. 200910167040.4, filed Aug. 17, 2009; the entire contents of which are incorporated herein by reference.

FIELD

Embodiments described herein relate generally to a medical head restraint for restraining the head of a patient (object) placed on the bed of a medical image diagnosis apparatus, radiotherapy apparatus, or the like at a predetermined position or in a predetermined state, and a medical bed system including the medical head restraint.

BACKGROUND

Assume that a region to be imaged or the like is the head of a patient in image diagnosis using a medical image diagnosis apparatus typified by X-ray computed tomography apparatuses, magnetic resonance imaging apparatuses, and the like or medical treatment using a radiotherapy apparatus or the like. In this case, a head restraint is used to restrain the head of the patient on the top of a bed at a predetermined position or in a predetermined state. When a region to be imaged or the like is, for example, a chest region, an abdominal region, or a region between an armpit and a knee, an arm up holder is used to prevent the arms of the patient on the top from overlapping the region to be imaged. A doctor or a medical technician selects such a head restraint or an arm up holder from various types of tools in accordance with the region to be imaged or the region to be treated.

Figure 1:
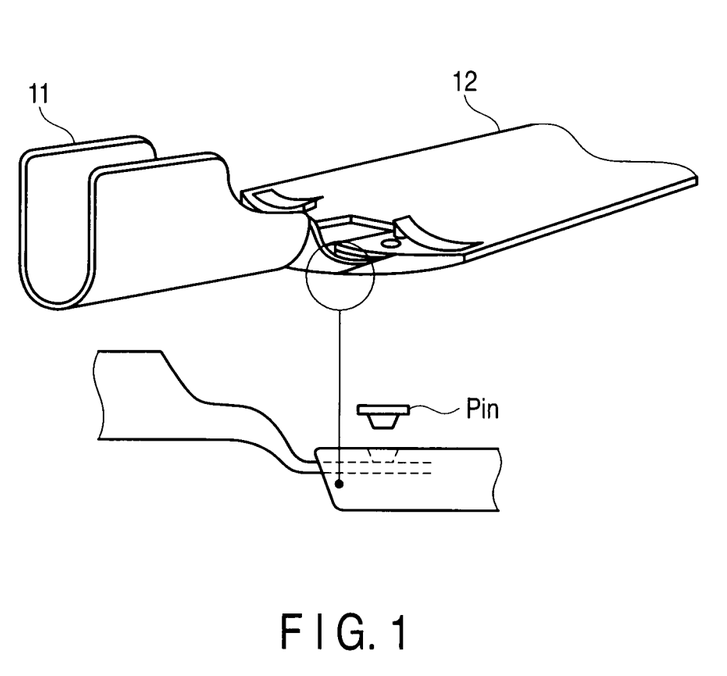
FIG. 1 is a view for explaining the structure of a conventional head restraint 11 provided for a top 12.
Figure 2:
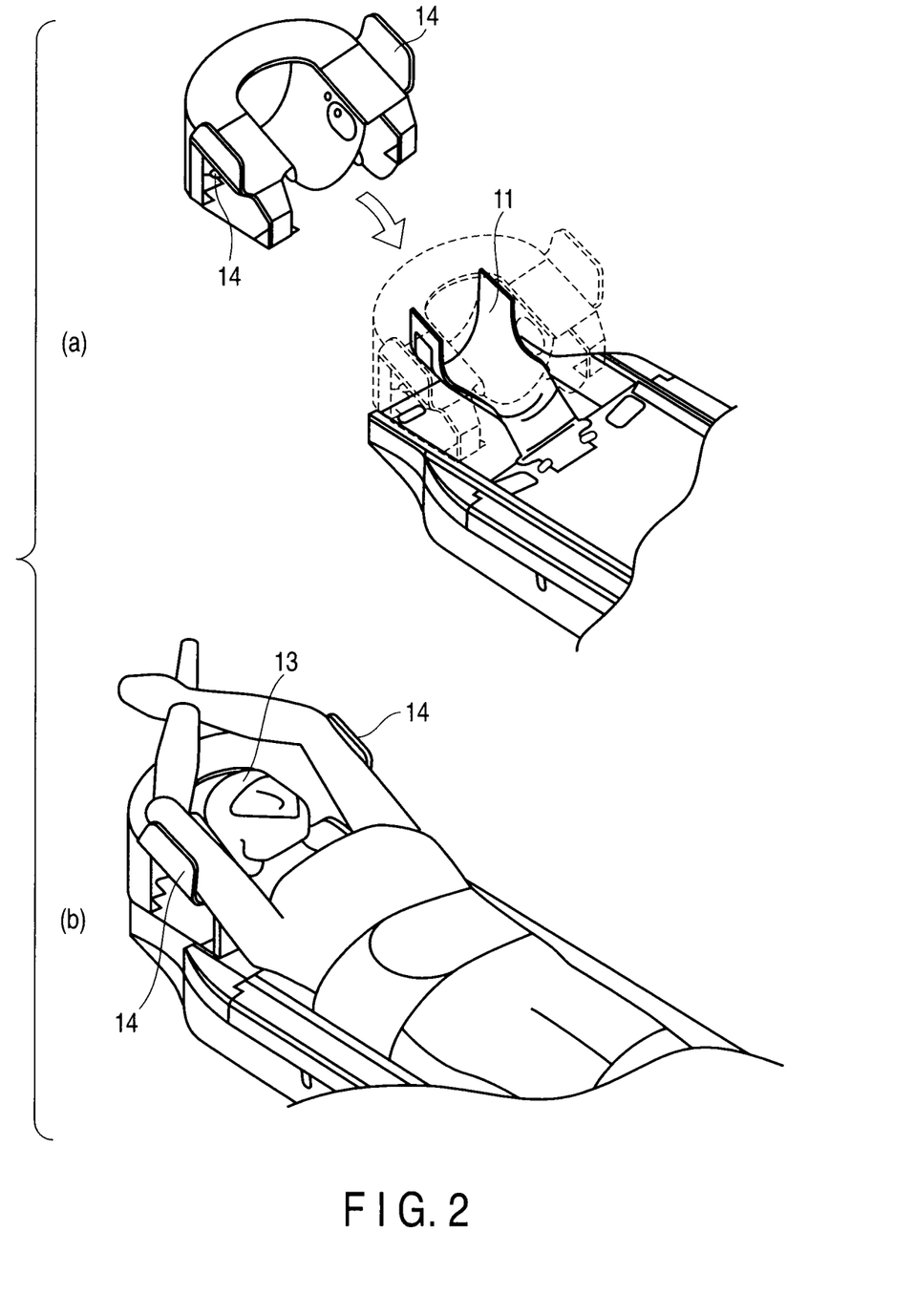
FIGS. 2(a) and 2(b) are views for explaining the conventional head restraint 11 and the arm up holder 14.

FIG. 1 is a view for explaining the structure of a conventional head restraint 11 provided for a top 12. FIG. 2 is a perspective view showing the state of the patient who is placed on the top 12 by using the conventional head restraint 11. As shown in FIG. 1, the head restraint 11 is partly inserted into the top 12 of the bed and fixed with a pin (or a hook) so as to be attached to the bed as an additional tool. A patient is placed on the top 12 such that the head or neck is placed on the head restraint 11 in conformity with its shape. When, for example, the head of a patient is to be imaged, the head is fixed on the head restraint 11 so as not to move by using a fixing band (hook-and-loop fastener) 13 which is prepared separately, as needed. When, for example, a chest region is to be imaged, an arm up holder 14 for supporting portions of the arms is attached to the head restraint 11, as shown in FIGS. 2(a) and 2(b).

A conventional head restraint 11 and arm up holder 14, however, have the following problems. That is, since the conventional arm up holder 14 is fixed in the state where it is partly laid on the head mount area of the head restraint 11, it is impossible to detach the arm up holder 14 unless the patient is raised from the top. When, therefore, performing whole body imaging or the like by using a contrast medium, for example, the doctor raises the patient and detaches the arm up holder 14 upon the head restraint 11, and then images a region other than the head. This imposes heavy loads on the doctor and the patient in imaging. In addition, in some cases, it is impossible to image a contrast medium flowing into each region at a proper timing. The arm up holder attached to the conventional head restraint is designed to support portions of the arms raised to a predetermined height. This gives a physical pain to an aged patient or the like who cannot raise his/her arms to a predetermined height. It is sometime impossible to properly perform imaging or the like.

DETAILED DESCRIPTION

An embodiment will be described below with reference to the views of the accompanying drawing. Note that the same reference numerals denote constituent elements having almost the same functions and arrangements, and a repetitive description will be made only when required.

Figure 3:
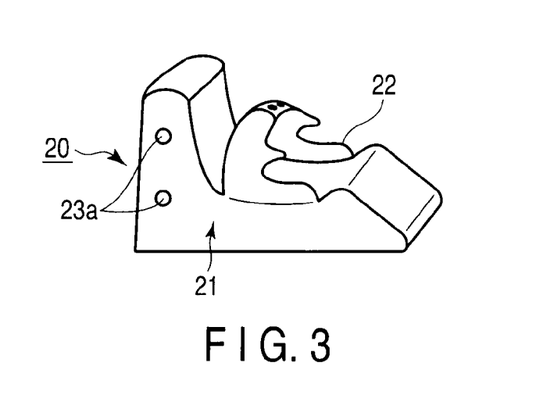
FIG. 3 is a perspective view showing an example of a head restraint 20 according to an embodiment.
Figure 4:
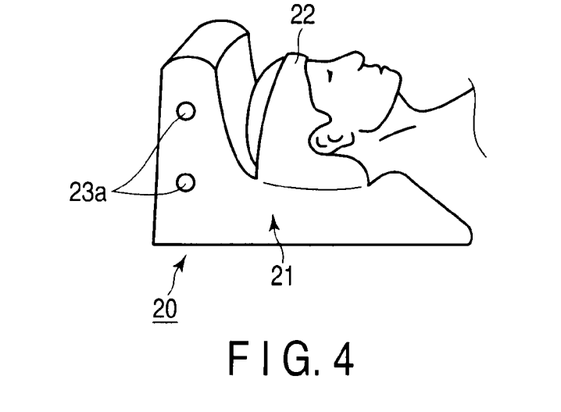
FIG. 4 is a perspective view showing a state in which the head is placed on the head restraint 20 according to the embodiment.
Figure 5:
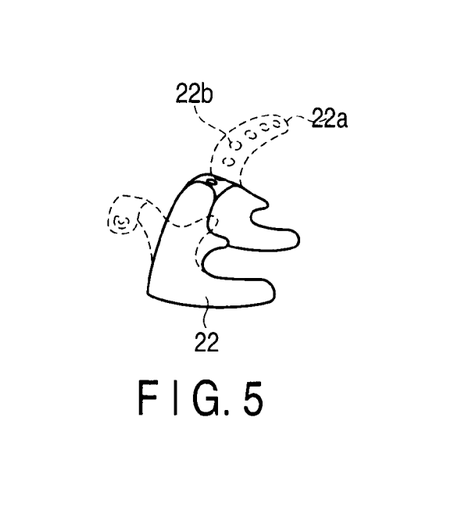
FIG. 5 is a perspective view for explaining the structure of the head holding portion of the head restraint 20 according to the embodiment.

FIG. 3 is a perspective view showing an example of a head restraint 20 according to this embodiment. FIG. 4 is a perspective view showing a state in which the head is placed on the head restraint 20 according to the embodiment. FIG. 5 is a perspective view for explaining the structure of a head holding portion 22 of the head restraint 20 according to the embodiment. As shown in FIGS. 3, 4, and 5, the head restraint 20 includes a headrest portion 21, the head holding portion 22, and insertion holes 23a formed in the headrest portion 21 to allow grip handles 23b (to be described later) to be inserted therein.

The headrest portion 21 is made of a high-density foamed material such as polyurethane, plastic, rubber, or the like, and has a shape conforming to a portion from the neck to the back of the head of a human body. As shown in FIG. 4, therefore, when the head of a patient is placed on the headrest portion 21 with the face upward, a portion from the neck to the back of the head of the patient is supported by the hardness of the well-fitting high-density foamed material. This allows the patient to comfortably receive image diagnosis or the like without feeling any physical load. In addition, the headrest portion 21 can be replaced with another headrest portion having a different size in accordance with the size of the head of a patient.

The head holding portion 22 has a structure to hold (or fix) the patient's head placed on the headrest portion 21. More specifically, as shown in FIG. 5, the head holding portion 22 includes a hook-like fixing tape 22a for fixing a patient's head on the headrest portion 21. The hook-like fixing tape 22a has a belt structure constituted by a belt buckle (not shown) and belt holes 22b. The hook-like fixing tape 22a is integrally formed with the head holding portion 22. When fixing a patient's head, therefore, it is not necessary to use any separate fixing tape as in the prior art. In addition, since the hook-like fixing tape 22a has a belt structure, it is possible to properly fix a patient's head on the headrest portion 21 regardless of the size of the patient's head. Obviously, the mechanism to fix a patient's head on the headrest portion 21 is not limited to the above belt structure. For example, it is possible to use a sheet tape or the like.

Figure 6:
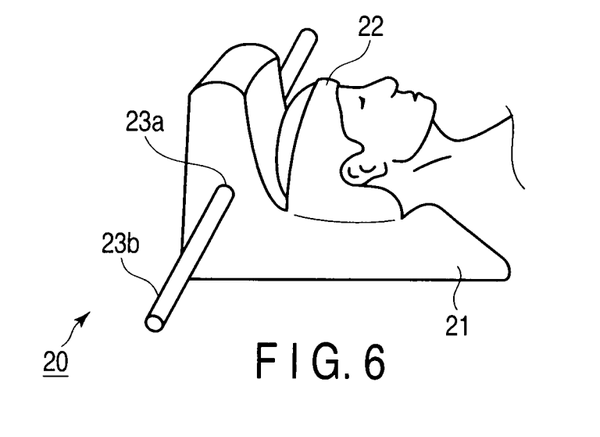
FIG. 6 is a perspective view for explaining the arm up holder of the head restraint 20.

A plurality of insertion holes 23a are provided such that at least the heights from the top of the bed or the distances from the vertex of the head placed on the headrest portion 21 differ from each other. As shown in FIG. 6, the grip handles 23b are inserted into some of the insertion holes 23a. The body position and size of a patient, how much the arms can be raised, and the like determine into which insertion holes 23a the grip handles 23b should be inserted. The insertion holes 23a and the grip handles 23b inserted in the insertion holes 23a form an arm up holder according to this embodiment. A patient holds the grip handles 23b inserted in the insertion holes 23a at a predetermined height. This allows the patient to comfortably keep raising the arms without feeling any physical load.

Figure 7:
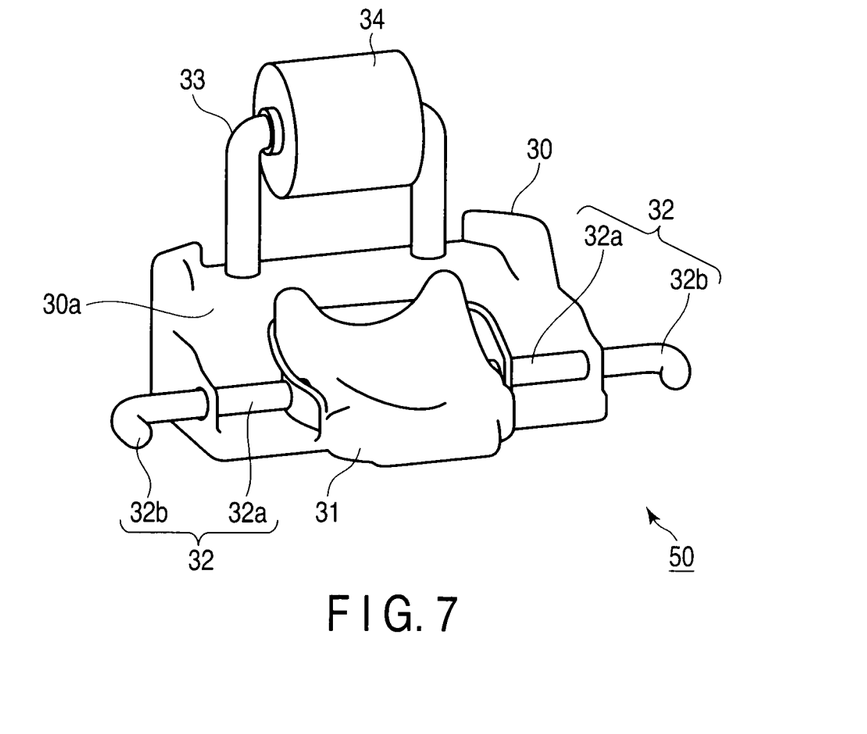
FIG. 7 is a perspective view showing a modification of the head restraint 20 according to this embodiment.

FIG. 7 is a perspective view showing a head restraint system 50 which is a modification of the head restraint 20 according to this embodiment. The head restraint system 50 according to this modification includes a base 30, a headrest portion 31, first hand holding portions 32, and second hand holding portions 33. The first hand holding portions 32 are grip handles extending through portions of the base 30 and the headrest portion 31. When a patient's head is placed on the headrest portion 31, the patient is made to hold the first hand holding portions 32. This allows the patient to keep raising his/her arms while placing his/her hands near the temples of the head. The second hand holding portions 33 are grip handles partly inserted in insertion holes formed in the base 30 near the vertex of the head. When the patient's head is placed on the headrest portion 31, the patient is made to hold the second hand holding portions 33. This allows the patient to keep raising his/her arms while placing his/her hands near the vertex of the head. Note that in the case shown in FIG. 7, the first hand holding portions 32 or the second hand holding portions 33 inserted in the insertion holes form an arm up holder.

Figure 8:
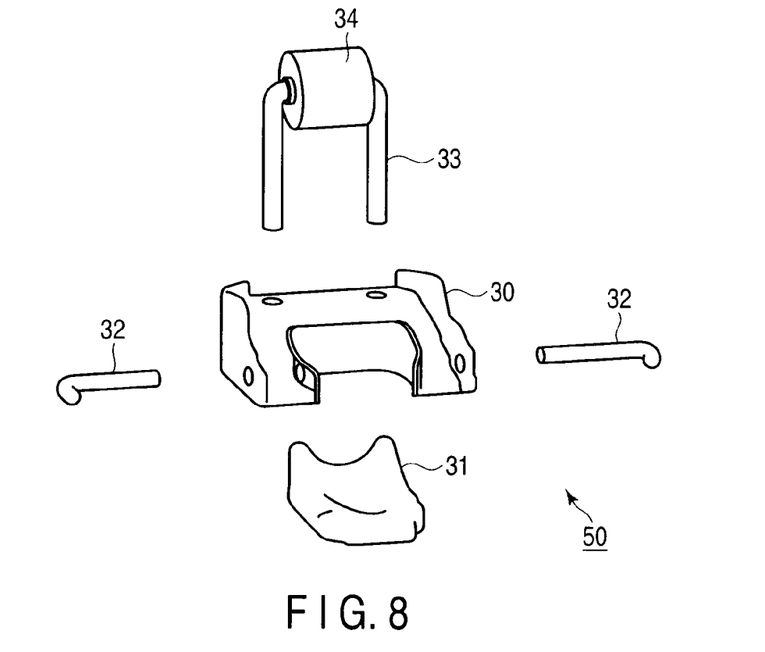
FIG. 8 is an exploded perspective view of the head restraint 20 shown in FIG. 7.
Figure 9:
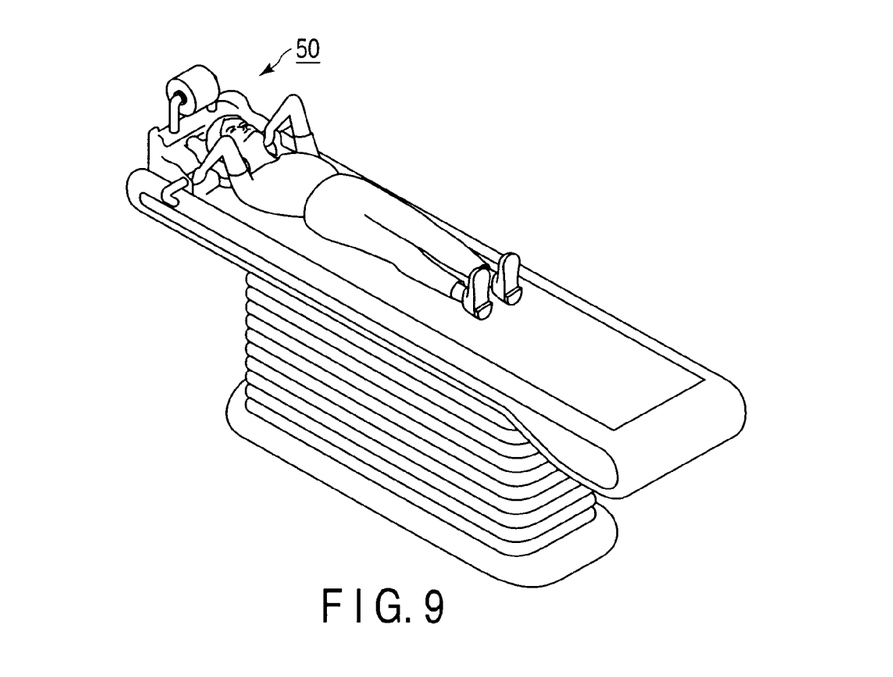
FIG. 9 is a perspective view showing an example of how a patient on the top holds first hand holding portions 32.

FIG. 8 is an exploded view of the head restraint 20 shown in FIG. 7. As shown in FIG. 8, the head restraint system 50 can be disassembled into the base 30, headrest portion 31, first hand holding portions 32, and second hand holding portions 33 (that is, they are detachable).

As shown in FIGS. 7 and 8, the head restraint system 50 according to this modification has the first hand holding portions 32 placed on the left and right sides of the headrest portion 31. Each of the first hand holding portions 32 on the left and right sides includes an inside holding portion 32a and an outside holding portion 32b. At the time of imaging, a patient can selectively hold any suitable portions of the above holding portions in accordance with the body position of the patient, how much the arms can be raised, and the like.

Figure 10:
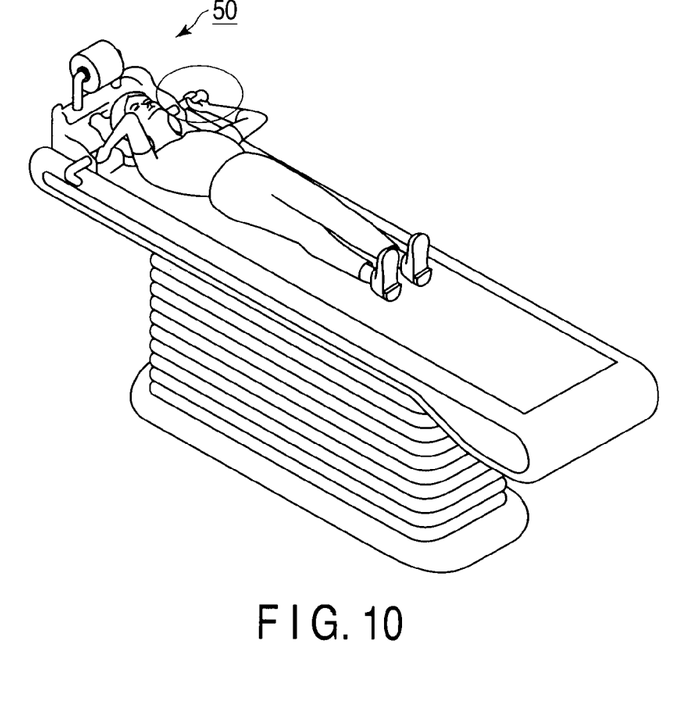
FIG. 10 is a perspective view showing another example of how the patient on the top holds the first hand holding portions 32.

More specifically, if an aged patient feels difficulty in horizontally rotating his/her shoulders, the patient can hold the inside holding portions 32a of the first hand holding portions 32 with both the left and right hands. Alternatively, as shown in FIG. 10, the patient can hold one of the inside holding portions 32a of the first hand holding portions 32 with one of the left and right hands while holding one of the outside holding portions 32b of the first hand holding portions 32 with the other hand. This can implement imaging while keeping the patient in a comfortable posture.

Figure 11:
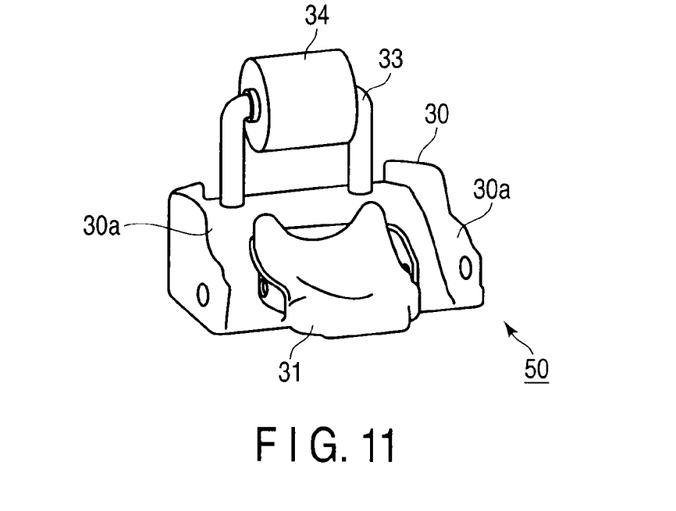
FIG. 11 is a perspective view showing the head restraint 20 including armrest portions 30a which allow the arms to be placed thereon.

In addition, if a patient feels difficulty in holding the first hand holding portions 32 with his/her hands, it is possible to detach the first hand holding portions 32 and directly support the arms by placing them on armrest portions 30a of the base 30, as shown in FIG. 11. The arrangement for permitting the first hand holding portions 32 to be detachable is practically useful even when imaging of the head has to be performed urgently and there is not a time long enough to set the first hand holding portions 32. In addition, the first hand holding portions 32 and the second hand holding portions 33 may cause scattered radiation when imaging of the head is performed. Therefore, the imaging is prevented from being adversely affected by such scattered radiation by detaching the first hand holding portions 32 and the second hand holding portions 33 when the imaging of the head is performed. Furthermore, the armrest portions 30a can be detached or raised, as needed.

Furthermore, as shown in FIG. 8, the head restraint system 50 can be disassembled into the base 30, headrest portion 31, first hand holding portions 32, and second hand holding portions 33. This makes it possible to select a combination of necessary components or detach unnecessary components in accordance with the region to be imaged or the region to be treated. For example, at the time of FF (Foot First) imaging, a patient is inserted into the gantry from his/her feet first (i.e., a region other than the head, e.g., the chest region, is imaged first, and the head is imaged lastly). In such a case, the head restraint system 50 is mounted on the top while the first hand holding portions 32 and the second hand holding portions 33 are placed on the headrest portion 31. After the chest region is imaged, it is possible to detach the first hand holding portions 32 and the second hand holding portions 33 from the headrest portion 31 without moving the patient and image the head using the head restraint system 50 attached with only the headrest portion 31.

Many patients are imaged and treated everyday by using medical image diagnosis apparatuses and medical treatment apparatuses. For this reason, high importance is placed on sanitary management for the bed and the head restraint system 50. As shown in FIGS. 7 to 12, the second hand holding portions 33 of the head restraint system 50 can be provided with disposable, exchangeable sanitary paper 34. Spreading the sanitary paper 34 on the headrest portion 31 can prevent oil and sebum of the hair of a patient from directly contacting the headrest portion 31. Even if sebum adheres to the bed or the head restraint system 50, it is possible to quickly wipe it off with the sanitary paper 34.

Figure 12:
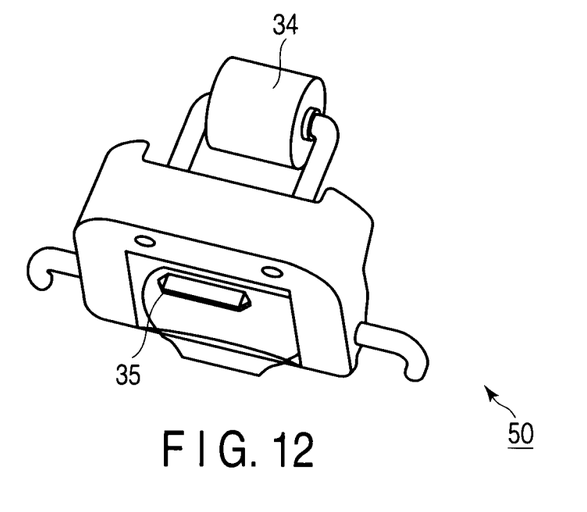
FIG. 12 is a perspective view of the head restraint 20 when viewed from below.
Figure 13:
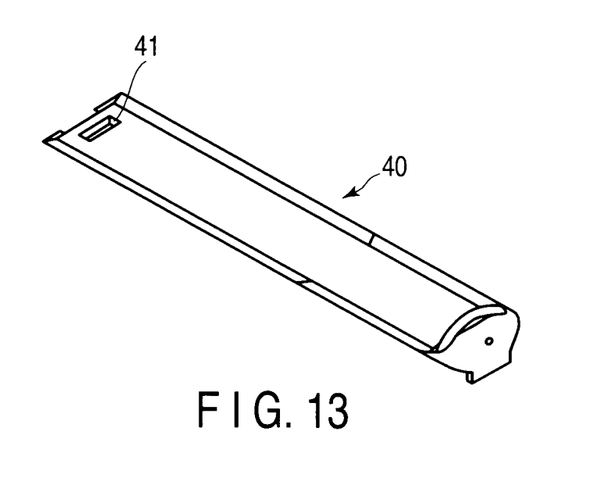
FIG. 13 is a perspective view of a top 40 of a bed on which the head restraint 20 is mounted.

FIG. 12 is a perspective view showing the head restraint system 50 when viewed from below. FIG. 13 is a perspective view of a top 40 of the bed installed on the head restraint system 50. When the head restraint system 50 is installed (attached) on the top 40, a convex portion 35 provided on the surface of the head restraint system 50 like that shown FIG. 12 which comes into contact with the top 40 is engaged with or fitted in a concave portion 41 of the top 40 like that shown in FIG. 13. The fixing direction of the convex portion 35 relative to the concave portion 41 is preferably the longitudinal direction of the top 40 from the viewpoint of horizontal symmetry and fixing strength. The user can fix the head restraint system 50 on the top 40 or detach the head restraint system 50 from the top 40 by moving the head restraint system 50 in the orthogonal direction to the top 40.

According to this arrangement, for example, lifting the head restraint system 50 in the vertical direction while slightly shifting it in the longitudinal direction of the top 40 can simply cancel the engaged (or fitted) state between the convex portion 35 and the concave portion 41. Therefore, it is possible to detach the base 30 etc. in the state where the head of a patient is kept on the head rest portion 31. The patient does not have to move the head away from the head rest portion 31 or sit up to change the body balance.

In addition, the head restraint system 50 can be quickly and easily detached from the top 40 regardless of the gap between the top 40 and the gantry of the medical image diagnosis apparatus or the angle of the top 40. In contrast to this, the conventional head restraint is configured to be partly inserted into the distal end of the top and fixed with a pin, and hence cannot be attached or detached depending on the width of the gap between the top 40 and the gantry or the angle of the top 40. Therefore, when the head restraint system 50 is to be detached from or attached to the top 40, there is no need to perform work such as securing a sufficient gap between the top 40 and the gantry by separating them from each other.

Note that this embodiment uses a fitting (engaging) mechanism shown in FIGS. 12 and 13 as a system for attaching the head restraint system 50 to the top 40. However, this mechanism is merely an example. That is, the head restraint can have any mechanism as long as it allows the head restraint to be installed on the top 40, instead of the structure of the head restraint which is configured to be partly inserted into the distal end of the top as in the prior art. In addition, the concave portion 41, which is part of an engaging (or fitting) mechanism, is located at an appropriate position on the top 40. Therefore, when the convex portion 35 is engaged with (or fitted in) the concave portion 41, and the head of the patient is placed on the head rest portion 31, the patient is automatically positioned.

According to the above arrangement, the following effects can be obtained. The head restraint system 50 according to this embodiment is configured such that the headrest portion is integrally formed with the arm up holder. When imaging the head of a patient, therefore, it is possible to properly fix the head so as to prevent it from moving by placing the head on the headrest portion and fixing it with a belt mechanism. When imaging the chest region of a patient, it is possible to allow the patient to keep raising his/her arms in a comfortable posture by holding the arm up holder in the same posture. When the head of a patient is imaged, the patient is only required to lie on the top of the bed while placing his/her head on the headrest portion 31. When the chest region of the patient needs to be imaged, the patient is only required to raise his/her hands and hold the arm up holder mounted on the headrest portion after imaging of the head. Therefore, even an aged patient who feels difficulty in raising his/her arms to a predetermined height can keep his/her suitable body position with a smaller load than in the prior art.

The head restraint according to this embodiment facilitates installation of the arm up holder by inserting the grip handles into the holes formed in the headrest portion, and allows the arm up holder to be easily detached by pulling the grip handles from the holes. When the arm up holder is attached or detached, there is no need to move the patient. This can reduce the work load on a doctor or the like at the stage of imaging or preparation for imaging.

In addition, it is possible to attach the head restraint according to this embodiment to the bed by engaging (or fitting) the concave portion of the upper portion of the bed with the convex portion attached to the surface of the head restraint located on the bed side. Canceling the engaged (or fitted) state can detach the head restraint from the bed. It is therefore possible to easily attach and detach the head restraint to and from the top of the bed in a space-saving manner even without a sufficient gap between the gantry of an imaging apparatus or treatment apparatus and the top. For this reason, when the head restraint is to be detached and attached and the arm up holder is to be detached and attached, there is no need to raise a lying patient or move the bed to secure a gap between an imaging apparatus and the gantry of a bed apparatus as in the prior art. This makes it possible to reduce the physical loads and work loads on patients, doctors, and the like at the stage of imaging or preparation for imaging (or at the stage of medical treatment or preparation for medical treatment) as compared with the prior art.

The head restraint according to this embodiment uses a high-density foamed material such as polyurethane, plastic, rubber, or the like for the portion on which the head of a patient is placed. Therefore, the patient can comfortably receive imaging or treatment without feeling any pain due to hardness. In addition, since the material is nonmetallic, this head restraint imposes no influence on images and has merits in terms of workability and cost.

Note that the present invention is not limited to the above embodiment, and constituent elements (e.g., the respective portions and parts) can be variously modified and embodied at the execution stage within the spirit and scope of the invention. Various inventions can be formed by proper combinations of a plurality of constituent elements disclosed in the above embodiments. For example, several constituent elements may be omitted from all the constituent elements in each embodiment. In addition, constituent elements of the different embodiments may be combined as needed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A head restraint attached on a top of a bed of one of a medical image diagnosis apparatus or a medical treatment apparatus, the head restraint comprising:
   a headrest portion configured to allow a head of an object to be placed directly thereon, a bottom of the headrest portion being a flat surface to be placed on top of a top surface of the bed, with the object being placed on the top of the bed, the headrest portion including a substantially vertical section and a substantially horizontal section; and
   an arm up holder including at least one handle for the object to hold, which handle is positioned on the top of the bed and in direct contact with the vertical section of the headrest portion to extend out transverse from both the vertical and horizontal sections of the headrest portion, and the at least one handle is positioned no lower than a bottom of the headrest portion and wherein the vertical section has opposing side surfaces defining a width and each of the at least one handle has a length greater than the width of the vertical section, and wherein each of the at least one handle extends outward from each of said opposing side surfaces.

2. The restraint according to claim 1, wherein the arm up holder is formed at a position where an elbow of the object is located above a shoulder of the object when the object placed on the top of the bed holds the at least one handle.

3. The restraint according to claim 1, wherein the arm up holder comprises
   a hole formed at a position corresponding to a position near a vertex of the head of the object when the head of the object is placed on the headrest portion, and
   the at least one handle is inserted into the hole.

4. The restraint according to claim 1, wherein the arm up holder comprises
   a hole formed at a position corresponding to a position near a temple of the head of the object when the head of the object is placed on the headrest portion, and
   the at least one handle is inserted into the hole.

5. The restraint according to claim 1, wherein the arm up holder comprises
   a plurality of holes which are formed at positions corresponding to a position near a vertex of the head of the object when the head of the object is placed on the headrest portion, and differ in at least one of a height from the top of the bed and a distance from the vertex of the head of the object, and
   the at least one handle is inserted into one of the plurality of holes.

6. The restraint according to claim 1, wherein the arm up holder comprises
   a plurality of holes which are formed at positions corresponding to a position near a temple of the head of the object when the head of the object is placed on the headrest portion, and differ in at least one of a height from the top of the bed and a distance from a vertex of the head of the object, and
   the at least one handle is inserted into one of the plurality of holes.

7. The restraint according to claim 1, the arm up holder is detachable from the headrest portion.

8. A medical bed system used for one of a medical image diagnosis apparatus or a medical treatment apparatus, the system comprising:
   a bed which includes a top configured to allow an object to be placed thereon;
   a headrest portion configured to allow a head of an object to be placed directly thereon, a bottom of the headrest portion being a flat surface to be placed on top of a top surface of the bed, with the object being placed on the top of the bed, the headrest portion including a substantially vertical section and a substantially horizontal section; and
   at least one handle for the object to hold, which handle is positioned on the top of the bed and in direct contact with the vertical section of the headrest portion to extend out transverse from both the vertical and horizontal sections of the headrest portion,
   and the at least one handle is positioned no lower than a bottom of the headrest portion and wherein the vertical section has opposing side surfaces defining a width and each of the at least one handle has a length greater than the width of the vertical section, and wherein each of the at least one handle extends outward from each of said opposing side surfaces.

9. The system according to claim 8, wherein the at least one handle is formed at a position where an elbow of the object is located above a shoulder of the object when the object placed on the top holds the at least one handle.

10. The system according to claim 8, wherein the headrest portion comprises
    a hole formed at a position corresponding to a position near a vertex of the head of the object when the head of the object is placed on the headrest portion, and
    the at least one handle is inserted into the hole.

11. The system according to claim 8, wherein the headrest portion comprises
    a hole formed at a position corresponding to a position near a temple of the head of the object when the head of the object is placed on the headrest portion, and
    the at least one handle is inserted into the hole.

12. The system according to claim 8, wherein headrest portion comprises
    a plurality of holes which are formed at positions corresponding to a position near a vertex of the head of the object when the head of the object is placed on the headrest portion, and differ in at least one of a height from the top and a distance from the vertex of the head of the object, and
    the at least one handle is inserted into one of the plurality of holes.

13. The system according to claim 8, wherein the headrest portion comprises
    a plurality of holes which are formed at positions corresponding to a position near a temple of the head of the object when the head of the object is placed on the headrest portion, and differ in at least one of a height from the top and a distance from a vertex of the head of the object, and
    the at least one handle is inserted into one of the plurality of holes.

14. The system according to claim 8, the handle is detachable from the headrest portion.

* * * * *